United States Patent [19]

Aginsky

[11] 4,204,531

[45] May 27, 1980

[54] INTRAMEDULLARY NAIL WITH EXPANDING MECHANISM

[76] Inventor: Yacov Aginsky, 18 Rachel St., Haifa, Israel

[21] Appl. No.: 970,830

[22] Filed: Dec. 19, 1978

[30] Foreign Application Priority Data

Dec. 28, 1977 [IL] Israel .......................................... 53703

[51] Int. Cl.$^2$ .......................... A61B 17/18; A61F 5/04
[52] U.S. Cl. .................................................. 128/92 BC
[58] Field of Search ........... 128/92 BC, 92 B, 92 BA, 128/92 BB, 92 R, 92 G; 3/1.9; 32/10 A

[56] References Cited

U.S. PATENT DOCUMENTS

| 3,759,257 | 9/1973 | Fischer et al. ................... 128/92 BC |
| 4,091,806 | 5/1978 | Aginsky ............................ 128/92 BC |

FOREIGN PATENT DOCUMENTS

| 2701279 | 7/1977 | Fed. Rep. of Germany ...... 128/92 BC |
| 587415 | 1/1959 | Italy .................................... 128/92 BA |

*Primary Examiner*—Ronald L. Frinks

*Attorney, Agent, or Firm*—Schwartz, Jeffery, Schwaab, Mack, Blumenthal & Koch

[57] ABSTRACT

An intramedullary nail comprising an outer tubular sheath and a rod-shaped element movable in the sheath in longitudinal direction, is provided at its front end, with an expandable element in the shape of two or more longitudinal spreadable branches formed out of the front end of the tubular sheath. An expanding mechanism comprises an expander heat provided at the front end of the rod-shaped element and two or more longitudinal links, one link each being pivotally connected at its rear end to one of the spreadable branches close to its front end and being, at its front end, pivotally connected to the expander head. After the nail has been inserted, front-end first, into the bone cavity, with its rear end protruding out of the bone, the expander head—together with the link ends—is pulled to the rear by outside manipulation of the rod-shaped element, whereby the links expand sideways and urge the branches towards the flared-out portion of the bone cavity, thus keeping the intramedullary nail in position within the bone.

11 Claims, 8 Drawing Figures

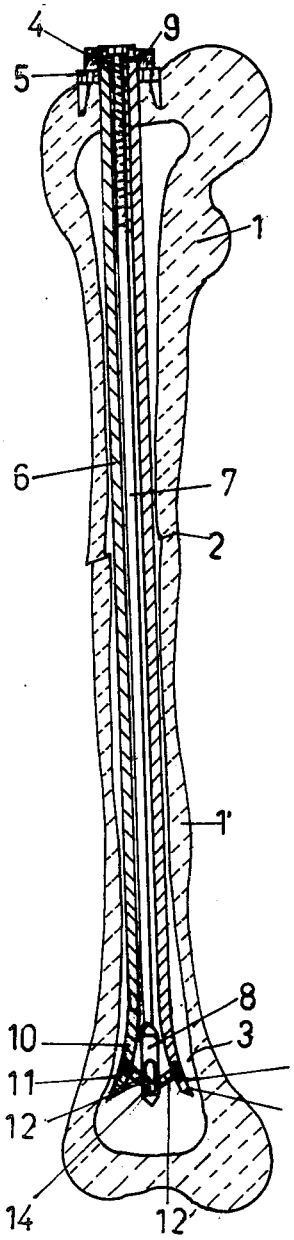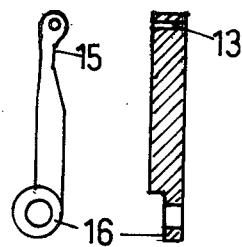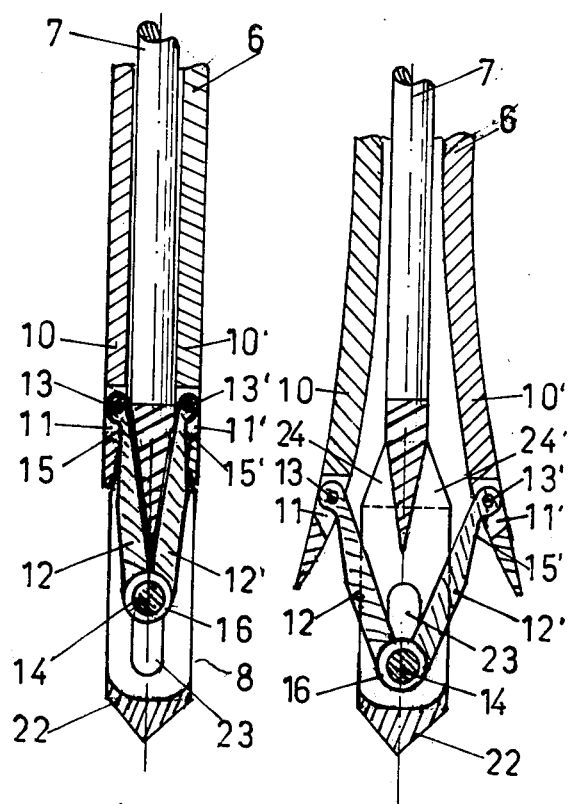
FIG.1.  FIG.2.  FIG.3.  FIG.4.  FIG.5.

INTRAMEDULLARY NAIL WITH EXPANDING MECHANISM

The invention relates to a supporting device for a fractured tubular bone instrumental in keeping the bone fragments aligned by its insertion into the medullary cavity of the bone. It relates more particularly to the expansion portion of such device which is to be placed into the flared-out portion of the cavity at the end of a femur or a similar bone. The expansion mechanism forms the front or leading end of either a so-called intramedullary compression nail used for jointing and compressing the relatively intact ends of the bone parts after a simple fracture, or of an intramedullary retraction nail used in keeping the two ends of a splintered bone aligned at the current distance, to promote healing and the formation of a new centre portion from and between splintered parts.

Various bone supporting devices are in use nowadays, all of them characterized by that the expansion mechanism comprises an expansible element in the form of spreadable branches of a longitudinally split tube, and an expander in the form of a wedge drawn in rearward direction in between the branches so as to spread these and to force them against the bone material of the cavity. Surgery of bone fractures by these means has been proved very successful, however it has been experienced that the outer ends of the branches are frequently bent inwardly beyond the elastic limit of the material, by the reactive pressure of the bone, whenever the wedge is drawn far to the rear to expand the branches sufficiently for intimate contact of branches and bone material. This bending is detrimental in two respects: —primarily, contact between the expanded portion and the bone cavity may not be sufficient to prevent longitudinal, lateral or angular movement of the nail in the medullary cavity, and secondly, the permanently bent ends prevent complete closing of the branches to their original diameter and may hinder withdrawal of the device after healing the fracture. Owing to the small diameter of the device, it is impossible to strengthen the branches, and in order to prevent their bending it is the object of the present invention to apply the force biasing the branches against the bone material, at or near their front ends; hereby inward bending will be avoided and the material will be not stressed beyond its elastic limit. As a result of this manner of spreading complete closing of the expansion portion of the device to its original diameter should be attained, thus enabling its ready and smooth withdrawal from the medullary cavity after complete rebuilding of the bone structure.

According to the invention, the expansion mechanism at the leading or front end of an intramedullary nail containing a tubular outer sheath and a rod-shaped element movable within the sheath in longitudinal direction, comprises an expansible element in the shape of at least two spreadable longitudinal branches formed out of the front end of the sheath by longitudinal slots extending rearward from the front end to a point defining the predetermined length of the branches; it further comprises at least two longitudinal links, each link being pivotally attached at its rear end to a point close to the front end of each branch, and being at its front end pivotally attached to an expander head formed at the front of the rod-shaped element. In a preferred embodiment of the invention the expander head is rigidly attached to the rod-shaped element, and has the form of a cylinder coaxial with the tubular sheath and of a diameter not exceeding the diameter of said sheath, which head is adapted to be positioned in front of the spreadable branches of the sheath in non-expanded or "closed" position of said branches. A preferred embodiment of the expansion mechanism contains only two branches with two links attached thereto, each to one branch end. The two links are pivotally interconnected at their front ends by an axle which has its ends supported by the expander head, either in a bore extending across the cylinder or in a longitudinal slot extending through the cylindrical part parallel to its axis. To accommodate the two links, the expander head is further provided, on opposite sides, at right angles to the longitudinal slot, with two grooves adapted to accomodate one link each in closed state of the expansion portion.

In the accompanying drawings which illustrate, by way of example, two embodiments of the invention, FIG. 1 is a longitudinal section through a bone and an intramedullary compression nail provided with an expansion mechanism according to the invention, FIG. 2 is a section through the expansion mechanism of FIG. 1 in closed state, FIG. 3 is a section through the expansion mechanism of FIG. 1 in expanded state, FIG. 4 is a side view of the link of FIG. 4

FIG. 5 is a longitudinal section through a link of the mechanism,

Figure 7:
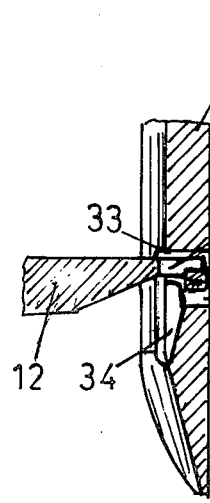
FIG. 7 is a section through a link and a branch, showing another embodiment of their interconnection.

With reference to FIG. 1 a thigh bone is shown to be broken into an upper part 1 and a lower part 1' along a fracture 2. An intramedullary compression nail is shown to have been driven into the bone cavity through a bore made in the upper part, and its expansion mechanism 3 at the front or leading end is shown to have been opened. The bone parts 1 and 1' are pressed together at the fractured faces 2 by means of a nut 4 threaded on a tubular sheath 6 of the nail through a spiked disc 5 in a manner known per se, which disc serves to prevent rotation of the nail.

With reference to FIGS. 1 to 5, the expansion mechanism of the compression nail—which likewise may form a part of a retraction device—comprises the symmetrical branches 10, 10' which are formed out of the front end of the tubular sheath 6 by a bifurcating longitudinal cut (not visible). Each branch is perforated near its front end by a cut-out 11, 11' in a suitable shape to accommodate the rear ends of connecting links 12, 12' and to connect these links to the branches by means of pins 13, 13' which latter pass through the said branches. The links are, at their front ends, shaped in the form of hubs 16 which are pivotally fastened on a common axle 14. Each hub is of half the width of the rest of the link resulting in that the total width of the two adjoining hubs does not exceed the width of each single link, which permits their moving in a common slot in the expander head as will be explained further below. The links are slightly recessed (15, 15') on their outside to permit the nesting therein of the branch ends.

Figure 6:
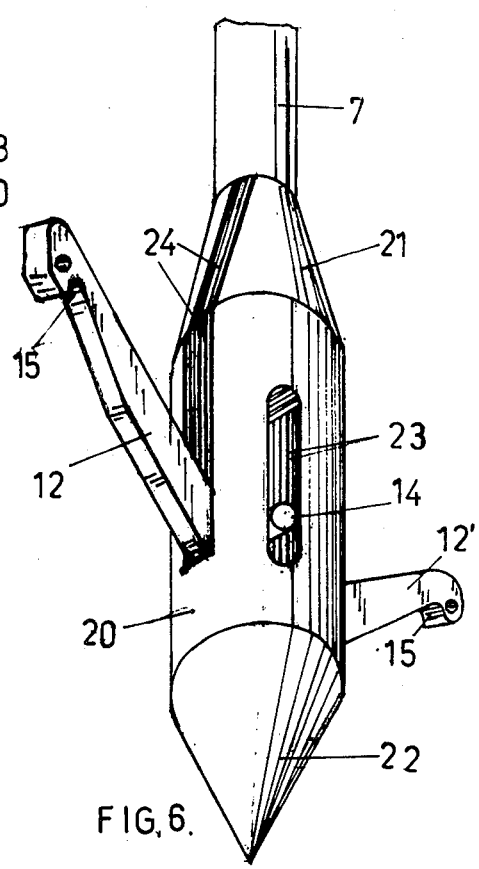
FIG. 6 is a perspective view of an expander head and two links of the mechanism, the branches not being shown.

The mechanism is operated from the outside, in a known manner, by a rod-shaped element 7 that can be moved in rearward direction to expand the branches against the bone cavity walls. Likewise it can be pushed in frontal direction to close the mechanism for withdrawal. For this purpose the rod 7 is enlarged at its front end to form an expander head 8 illustrated in detail in FIG. 6. The head 8 is in the shape of a cylinder 20 connected to the rod 7 by a conical neck 21; its front end is pointed in the form of a cone 22 to facilitate its entry into the intramedullary cavity and its penetration through the bone marrow. The cylindrical part is perforated by a through-going slot 23 of a width permitting free movement in axial direction of the axle 14 and the links mounted thereon, and of a length of about half the length of the cylindrical portion. The grooves 24, 24'—of a width somewhat wider than the width of each link 12—are cut out of the cylinder and the conical neck 21, at right angles to the slot 23, and serve to accommodate the links in closed position of the device.

The working mechanism is demonstrated in FIGS. 2 and 3:—in closed state the rod and the expander head are in their foremost position with the axle 14 positioned at the rear end of the slot 23. Hereby the links are stretched and folded together inside the grooves 24, 24', and the two branches 10, 10' extend in continuation of the outer sheath 6. In this state the device can be driven into the intramedullary cavity of the bone. After its insertion the rod 7 is pulled to the rear by means of a rotatable, threaded tube 9 in a known manner and the expander head is moved in between the two branches 10, the conical neck spreading them slightly. Further retraction of the rod 7 moves the axle 14 to the front end of the slot 23 whereby the two links 12, 12' are spread apart and, on their part, expand the branches against the cavity walls of the bone (FIGS. 1 and 3).

In order not to overstress the bone material the moment enacted from the outside is controlled, for instance by a torque wrench, permitting the surgeon to stop the expansion at the correct moment. Now the two broken bone parts are pulled together by means of the nut 4, in a known manner, until the bone and the nail form one rigid unit. After healing of the fracture, the process is reversed:—the expander head is pushed in frontal direction pulling links and the branches into the closed position as per FIG. 2. In this state the nail can be readily withdrawn from the bone cavity.

The main advantages of the present invention are:—1. the branches cannot be bent inwardly at their tops or front ends, which ensures their complete closing to their original diameter for withdrawal and enables firm gripping of the cavity walls. 2. Their closing is not dependent on their resilience as with the known devices wherein the branches are spread by a wedge and are supported to close tightly after the wedge has been withdrawn from in between the branches; in the present embodiment they are closed by a positive force enacted on them by the axle 14 while this is driven in forward direction. For clearer understanding of the invention a mechanism with two branches only has been illustrated and described in the foregoing, but it is understood that the mechanism may be built to have three or four branches with three or four links actuating them, the expander head being suitably modified by a person skilled in the art.

It is also proposed to dispense with the slot 23 altogether and to mount the axle 14 in a throughgoing transverse bore. In this case the spreading of the branches is not started by action of the conical neck, but by the spreading of the two links—which are to be made somewhat longer than in the aforedescribed embodiment. As an alternative, the two branches may be longitudinally slotted, the pins 13 moving along the branches in said slots with the like effect as obtained by the slot 23.

Instead of connecting the link and the branch by means of a pin, this connection may be made by a bulb-like enlargement 30 at the end of the link 12, engaging with a rectangular recess 31 on the outside of the branch 10. The enlargement is separated from the main part of the link 12 by a narrow neck 32, which penetrates through a rectangular hole 33 in the branch. The inside of the branch is obliquely recessed (34) to accomodate the link in closed position of the device.

Figure 8:
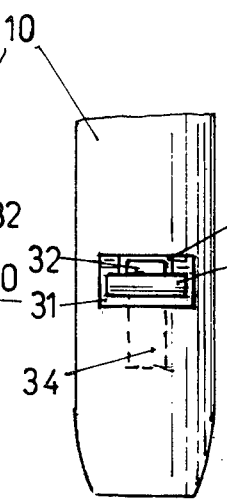
FIG. 8 is a side view of the branch and the link shown in FIG. 7.

Operation of the expanding mechanism comprising the connection as illustrated in FIGS. 7 and 8 is identical with the aforedescribed operation. The connection may likewise be employed for the connection of more than two links and branches of one mechanism.

The expanding mechanism has been, up to now, described and illustrated in connection with an intramedullary compression nail only, wherein the rod (7) is retracted by means of a threaded tube. It will, however, be understood that the same mechanism may be utilized with any type of intramedullary nail or bone supporting device, and that the longitudinal motion of the rod-shaped element (7) may be induced by any other known mechanism.

In spite of the fact that the mechanism built in accordance with the invention requires more components and more intricate parts than the known devices, nevertheless the advantages are sufficient to warrant the additional costs.

Only two embodiments of the links and the expander head have been described and illustrated in this specification, but it is obvious that the links, the branches and the expander head may be interconnected by other mechanical means, such modifications to be carried out by a person skilled in the art within the scope of the appended claims and other spirit of the invention.

I claim:

1. An expanding mechanism of an intramedullary nail, the latter containing a tubular outer sheath and a rod-shaped element movable in said sheath in longitudinal direction, the expanding mechanism having a front portion to be driven head first into the cavity of a fractured bone and a rear portion forming a continuation of the said outer sheath and said rod-shaped element, the mechanism comprising an expansible element in the shape of at least two longitudinal spreadable branches formed out of the front end of said tubular sheath and at least two longitudinal links, each link being pivotally connected at its rear end to one of said branches at a point close to the front end of said branch, and being pivotally connected at its front end to an expander head pivoted at the front of said rod-shaped element.

2. An expanding mechanism as defined in claim 1, wherein said spreadable branches are formed out of said tubular sheath by longitudinal slots extending from the front end of said sheath to a point to the rear defining the predetermined length of said branches.

3. An expanding mechanism as defined in claim 1, comprising an expander head rigidly attached to the front end of said rod-shaped element, in the form of a cylinder co-axial with said tubular sheath and of a diameter not exceeding the diameter of said sheath, adapted to be positioned to the front of said branches in non-expanded or "closed" position of the expanding mechanism.

4. An expanding mechanism as defined in claim 2, comprising two symmetrical branches formed out of the said tubular sheath by one bifurcating cut starting from the front end to a point to the rear defining the length of said branches.

5. An expanding mechanism as defined in claim 4, comprising two links each of which is, at its rear end, connected to one of the two branches by a pin passing transversely through the branch and the link.

6. An expanding mechanism as defined in claim 4, comprising two links the front ends of which are connected to each other and to said expander head by an axle passing transversely through said links and through said expander head.

7. An expanding mechanism as defined in claim 6, wherein said axle connecting said links is fixed in a transverse bore in the expander head.

8. An expanding mechanism as defined in claim 6, wherein said axle is accommodated and movable in the direction of the nail axis in a slot extending across said expander head.

9. An expanding mechanism as defined in claim 3, wherein said expander head is integral with said rod-shaped element and connected thereto by a conical neck.

10. An expanding mechanism as defined in claim 3, wherein said expander head is provided with a conical pointed front end.

11. An expanding mechanism as defined in claim 8, wherein said expander head is provided with two opposite grooves corresponding in width and depth to the dimensions of said two links, the grooves being arranged at right angles to said slot accomodating said axle.

* * * * *